United States Patent [19]
Persson

[11] Patent Number: 5,993,214
[45] Date of Patent: *Nov. 30, 1999

[54] METHOD FOR MANUFACTURE OF A DENTAL PRODUCT

[75] Inventor: Magnus Persson, Vanersborg, Sweden

[73] Assignee: Nobel Biocare AB, Gothenburg, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/652,503
[22] PCT Filed: Oct. 3, 1995
[86] PCT No.: PCT/SE95/01130
  § 371 Date: Jul. 31, 1996
  § 102(e) Date: Jul. 31, 1996
[87] PCT Pub. No.: WO96/10370
  PCT Pub. Date: Apr. 11, 1996

[30] Foreign Application Priority Data

Oct. 4, 1994 [SE] Sweden .................................. 9403346

[51] Int. Cl.⁶ ............................................... A61C 5/10
[52] U.S. Cl. ............................................ 433/223; 433/215
[58] Field of Search .................................. 433/223, 226, 433/215, 213, 214, 222.1

[56] References Cited

U.S. PATENT DOCUMENTS

| | | |
|---|---|---|
| 4,104,798 | 8/1978 | Takahashi et al. .................... 433/222.1 |
| 4,746,532 | 5/1988 | Suzuki et al. .............................. 623/16 |
| 4,937,928 | 7/1990 | Van Der Zel ............................ 433/223 |
| 5,288,232 | 2/1994 | Panzera et al. ....................... 433/222.1 |
| 5,289,468 | 2/1994 | Yoshida .................................. 370/85.13 |
| 5,387,247 | 2/1995 | Vallana et al. ............................. 623/66 |
| 5,391,841 | 2/1995 | Quick ....................................... 174/258 |
| 5,440,496 | 8/1995 | Andersson et al. ................. 364/474.05 |
| 5,441,536 | 8/1995 | Aoki et al. ............................... 427/2.27 |
| 5,607,305 | 3/1997 | Andersson et al. ...................... 433/223 |

Primary Examiner—John J. Wilson
Attorney, Agent, or Firm—Pollock, Vande Sande & Amernick

[57] ABSTRACT

A method for the manufacture of a product such as a dental product or product intended for use in the human body and comprising a substructure of titanium or equivalent tissue-compatible material and intended for coating with a ceramic onlay material, comprises (a) transferring information ($i_5$), preferably via the tele-communications network from a client, concerning the construction of the product, and manufacture of the substructure at the production site, and also information concerning the transfer or return, of the product to the coating site for the ceramic onlay material or to the client, (b) including in the information transfer implementation of data that the substructure or the product is to be coated with one or more plasma layers compatible with the material of the substructure/product, and (c) providing the production site with a station in which the plasma layers are applied by a plasma application installation which is activated as a function of the data.

8 Claims, 2 Drawing Sheets

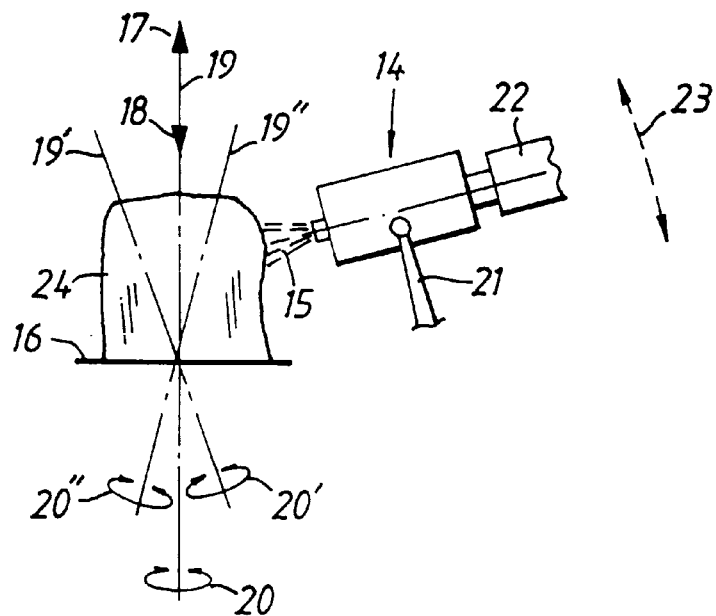
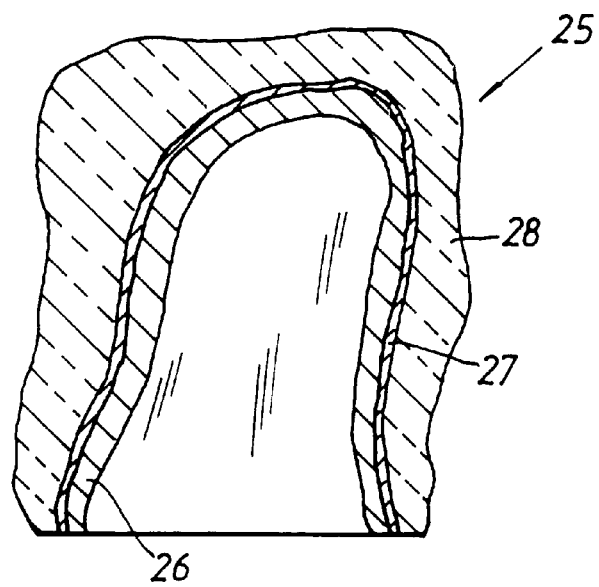

METHOD FOR MANUFACTURE OF A DENTAL PRODUCT

FIELD OF THE INVENTION

The present invention relates to a method for the manufacture of a product such as a dental product, or a product for use in the human body and formed of with a sub-structure of titanium or other equivalent tissue-compatible material. The substructure is intended to be coated with ceramic onlay material (porcelain).

The present method includes information transfer, preferably via a telecommunications network, from a client.

The information may include data on the construction of the product. The method also includes the manufacture of the said substructure at the production site, and as the transfer or return of the product to the coating site for the ceramic onlay material or to the client.

The invention also relates to a device for facilitating application of ceramic onlay material, onto a product which is made of titanium, or equivalent tissue-compatible material and intended for dental or bodily purposes.

The invention furthermore relates to a product for use in a dental or other bodily context. A possible example of a product is a dental cap. The product comprises a substructure made of titanium or other tissue-compatible material which is intended to support one or more ceramic onlays.

BACKGROUND OF THE INVENTION

It is already known to use a transmission medium, for example a public telephone network, to transfer digital information on the construction of various dental products. With the aid of the information transfer, a dentist, dental technician, etc., can, in this case, request a machining site to produce a given dental product. It is also known to produce dental caps, dental bridge parts, etc., centrally, these being made of titanium or other tissue-compatible material. The production, which generally involves the milling of titanium material, is relatively complicated and requires complex technology which may not be available to the client. The product in question can, in this case, be regarded as a semi-finished product and returned to the client for further handling. For example, the client may coat the product in question with a ceramic material forming an onlay corresponding to a replacement tooth or the like.

The transfer of information to the central machining site is effected by an information loop which can include machining data, address data for the sender and the recipient, desired delivery date, etc.

It is already known, in the case of implants intended to become incorporated in the dentine, to provide the implant with a thin plasma layer of ceramic material which is intended to facilitate the incorporation of the implant into the dentine. It is thus already known to use plasma spray installations in conjunction with implants of this type.

SUMMARY OF THE INVENTION

Applying onlay material (ceramic) onto a product substructure which has been produced in this way is a relatively complicated procedure. The application is effected in different layers. It is difficult to get the porcelain, or the ceramic, to attach to the titanium, among other reasons because it is necessary to work at relatively low temperatures. The invention aims to solve this problem and proposes a method and device, and also a product, allowing the application of the onlay material to be considerably simplified for the customer and client.

There is also the problem of achieving an aesthetic covering of the substructure when applying the porcelain.

The titanium is dark and shows through the onlay material, especially if the latter is to be coated with a thin layer. The invention also solves this problem.

The feature which can principally be regarded as being characteristic of the novel method is that the information transfer includes implementation of data concerning the fact that the substructure or the product is to be coated with one or more plasma layers compatible with the material of the substructure/product. The production site in question is, in such case, equipped with a station in which the plasma layers can be applied by means of a plasma application installation which is activated as a function of the data.

A device according to the invention can principally be regarded as being characterized in that it comprises support members for the product, and plasma application members for applying a plasma layer to the product. Also included is equipment which initiates reciprocal movements between the support member/product and the plasma installation. The equipment can be activated using activation information, and when such activation information is supplied to the equipment, coating of one or more plasma layers onto the substructure takes place.

The feature which can principally be regarded as characterizing a product according to the invention is that the substructure is coated with a plasma layer compatible with the material of the substructure, and with the material of each ceramic onlay applied to the structure, for the purpose of facilitating application of the onlay material for a customer or client who has ordered the product. In one embodiment, the plasma layer can have a thickness of approximately 200 micrometers. The plasma layer is applied on those parts which do not interact with the dentine or a corresponding part of the human body.

By means of what has been proposed above, controlled, thin plasma layers can be obtained on the respective product. The plasma layer material is preferably of a color which does not show through the onlay material. The layer in question considerably facilitates the application of the onlay material.

Equipment which is known can be used for the plasma layer application. The application of the plasma layer can take place at temperatures which are considerably higher than the fusion temperature or the phase transition temperature of the titanium. Plasma-sprayable ceramics which are known can be used on condition that they are compatible with the titanium material and with the onlay material. Aesthetically advantageous onlays can be obtained for, or by, the customer or the client in a much simpler way than has hitherto been possible. By means of the invention, the previous manual handling during the application of onlay material can be considerably reduced and simplified. Uncertainty in the application procedure can thus be eliminated. One advantage is that the plasma layer application takes place centrally, since expensive and relatively complicated equipment has to be used. It is also advantageous to arrange the application operation at a site where a large number of products can be processed.

BRIEF DESCRIPTION OF THE DRAWINGS

A presently proposed embodiment of the method, device and product having the characteristic features of the invention will be described hereinbelow, time with reference to the attached drawings in which:

FIG. 3 shows, in a side view, parts of the plasma layer application equipment in conjunction with a product, in the form of a dental cap substructure, arranged on a rotating platform, and FIG. 4 shows a vertical cross-section of a product with onlay material applied.

DETAILED DESCRIPTION OF THE PREFERRED EMBODIMENT

Figure 1:
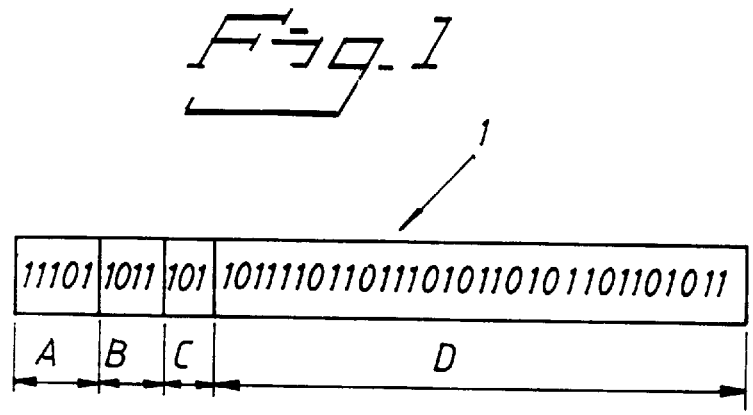
FIG. 1 shows, in diagram a form, an information loop or an information packet relating to an order for production of an identified product.

In FIG. 1, reference 1 shows an information loop made of different parts A, B, C and D. The information contains data A on the addressee, for example a central production unit. Also included is data B on the client, the desired delivery date, etc. In accordance with the present invention, an information section C is also included, concerning whether the product or part thereof is to be coated with a plasma layer according to what is stated below. The data in space C can, in this case, include the thickness of the plasma layer, the color of the plasma layer, the number of plasma layers, etc. There is also included, in a known manner, an information section D which includes production data for the product in question. The information can be digital and can consist of "ones" and "noughts" in a known manner.

Figure 2:
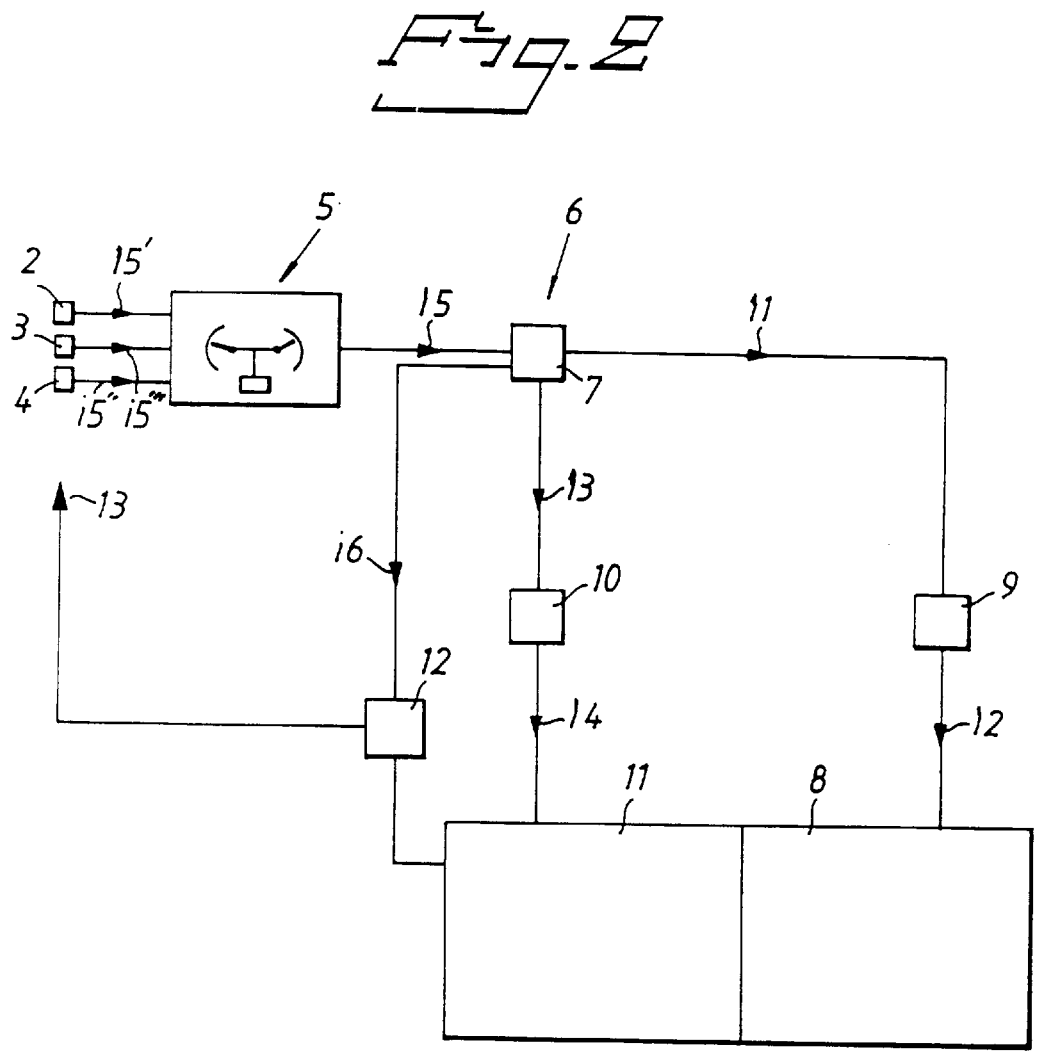
FIG. 2 shows, in a block diagram form, information transfer via a telecommunications medium to a central unit which receives the production information and includes a station for milling of the product and a station for plasma layer application to the product or a part thereof.

According to FIG. 2, a number of customers 2, 3 and 4 can use a telephone network, for example the public telephone network 5, to communicate with a producer 6 or production location. The telecommunications system can in this case operate with so-called packet transmission of known type, in which information from each client is transported via combinable packets to the producer 6. The customers have, in a known manner, modems which are used during the transfer, and the production station or equivalent has members 7 which can extract and identify the information items from the customers 2, 3, 4 in a manner which is likewise known per In accordance with the concept of the invention, the production location can include one or more stations 8 for milling of products or product parts in a known manner. The information distinguished in the unit 7 is received in a unit 9 for generating guidance coordinates which are used in conjunction with the machining or production of the product. The machining and the manufacture of the product, for example a dental cap, can be carried out in a known manner and will therefore not be described in any detail here.

According to the invention, the product or product part manufactured in each production station will be coated with a plasma layer, in accordance with what is stated below, if information C (see FIG. 1) is present in connection with the order. The information according to C is distinguished in the unit 7 and is received in a unit 10 which generates guidance coordinates and/or guidance information for a plasma layer coating installation 11 which can be arranged in connection with the production station or the production stations 8 or can be separate from these.

In FIG. 2, the information concerning the actual production itself is indicated by $i_3$, while milling coordinates which have been compiled are represented by $i_2$. In a corresponding manner, the information C emanating from the unit 7 is indicated by $i_3$, while the machining function from the unit 10 has the designation $i_4$. The total information input to the production unit is indicated by $i_5$, which thus includes data according to A, B, C and D. Address information relating to the client is stored in a unit 12, and the address information is represented by $i_6$. Products manufactured in stations 8 and 11 are thus addressed in the unit 12. The products are then returned 13 to the clients 2, 3 and 4, or to the location specified by each client, for building up the products with onlay material. The order information from the clients is indicated by $i_{5'}$, $i_{5''}$ and $i_{5'''}$.

FIG. 3 shows equipment 14 for spraying on plasma layers. The equipment 14 can be of a known type and operates using the known plasma application principle. Starting material being sprayed on is indicated by 15. The product in question, which has been manufactured in accordance with the above at the station or stations 8, is set up on a support platform 16, for example a rotating platform. The platform 16 can be of the type which can be raised and lowered in the directions of the arrows 17 and 18. The longitudinal axis of the rotating platform is indicated by 19. The rotating platform can in this case be of the type where the platform is tiltable, i.e. the longitudinal axis 19 assumes different directions 19', 19", etc. The rotational movements of the platform are indicated by 20, 20' and 20", respectively. Alternatively, or in addition, the plasma spray device can be arranged in a fixed or movable manner.

A bearing arrangement is indicated by 21, and a ceramic or powder container by 22. Tilting movements of the equipment are indicated by broken-line arrows 23. A product placed on the platform is shown by 24. The rotating platform can be rotated at a speed which can lie between 100 and 500 revolutions per minute. The plasma spray equipment can in this case operate with a material delivery 15 which gives one or more applied layers of 100 to 300, preferably approximately 200, micrometers in thickness. Rotations, upward and downward movements, and any movements of the assembly 14 can in this case take place simultaneously.

FIG. 4 shows a tooth replacement or crown indicated by 25. The tooth replacement comprises a product 26 which is manufactured at the station or stations 8 in accordance with the above. The product or the substructure 26 has a spray-coated plasma layer 27 which has been shown in a greatly enlarged form for the sake of clarity. Onlay material 28 of a known type is applied on top of the layer. 27 represents a controlled layer of ceramic which is known, for example alumina. Alternatively, the layer can consist of a mixture of ceramics. The layer can be grey, for example, and covers the material surface/titanium surface of the substructure 26. The layer 27 has a coefficient of thermal expansion which is compatible both with the substructure material 26 and with the onlay material 28, which too can be made up of ceramics which are known. In addition to the fact that the application of the material 28 is considerably simplified, the dark surface of the substructure 26 is eliminated with the aid of the grey or differently colored layer 27. The application of the layer 27 can take place at several hundred degrees or at a temperature considerably above the fusion temperature of the material/titanium of the substructure 26. In the spray installation, the material 27 is present in powder form, which can be purchased in the open market. The application thus takes place in a separate production stage. The plasma-sprayable ceramic is sprayed through a hot arc in a manner known.

Preferably, the equipment at the stations 8 and 11 is, in the main, completely automated.

The invention is not limited to the embodiment shown hereinabove by way of example, and can instead be subjected to modifications within the scope of the following patent claims and the inventive concept.

I claim:

1. A method for producing a dental product at at least two sites, said product intended to be coated with ceramic onlay material and made from a tissue compatible material, said method comprising the steps of:

transferring information data from a client to a production site, said information data representing the construction of said product, the manufacturing of a substructure of said product, the coating of said substructure with at least one plasma layer compatible with said substructure, and transfer of said product to a second site;

producing said substructure with production equipment at said production site based on said information data;

coating said substructure with said at least one plasma layer at said production site as a function of said information, wherein said information comprises data relating to a predetermined shape of said substructure whereby said substructure is prepared to receive said ceramic onlay;

transferring said product to a second site based on said information;

applying said ceramic onlay material at said second site and upon activation ($i_4$), initiating rapid reciprocal movements between the product and a plasma application installation with each applied plasma layer assuming a thickness of 100 to 300 micrometers.

2. A method according to claim 1, wherein the production equipment and the plasma application equipment are completely automated in the main.

3. A method according to claims 1, wherein the product is rotated and pivotable in the plasma application installation which includes a stationary plasma spray member.

4. A method according to claim 1, wherein said plasma application installation includes a rotatable and pivotable plasma spray member and said product is kept stationary.

5. The method according to claim 1 wherein said information is in one or more packet frames, a first packet for the production site, a second packet for client data, a third packet for plasma coating information, and a fourth packet for production data.

6. The method according to claim 5 further comprising the steps of:

receiving said information with a modem at said production site; and extracting said packet frames from said information with an extraction member.

7. The method according to claim 1 wherein said plasma coating information comprises data relating to the thickness, color, and number of plasma layers.

8. A method for producing a dental product at at least two sites, said product intended to be coated with ceramic onlay material and made from a tissue compatible material, said method comprising the steps of:

transferring an information packet from a client to a production site via a telecommunication network, said information packet comprising an addressee data frame, a client data frame, a plasma application data frame, and a production data frame; at said production site:

extracting said production data;

manufacturing a substructure of said product based on said production data;

extracting said plasma application data;

coating said substructure with one or more plasma layers based on said plasma application data to achieve a predetermined shape;

transferring said product to said second site based on said client data; at said second site, coating said product with said ceramic onlay material and upon activation ($i_4$), initiating rapid reciprocal movements between the product and a plasma application installation with each applied plasma layer assuming a thickness of 100 to 300 micrometers.

* * * * *